United States Patent
Haefner et al.

(10) Patent No.: US 8,393,234 B2
(45) Date of Patent: Mar. 12, 2013

(54) APPARATUS, DEVICE AND METHOD FOR ARRANGING AT LEAST ONE SAMPLE CONTAINER

(75) Inventors: Peter Haefner, Neuenbuerg (DE); Bernd Hutter, Engelsbrand (DE)

(73) Assignee: Berthold Technologies GmbH & Co. KG, Bad Wildbad (DE)

( * ) Notice: Subject to any disclaimer, the term of this patent is extended or adjusted under 35 U.S.C. 154(b) by 34 days.

(21) Appl. No.: 13/025,574

(22) Filed: Feb. 11, 2011

(65) Prior Publication Data

US 2012/0036918 A1 Feb. 16, 2012

(30) Foreign Application Priority Data

Aug. 13, 2010 (EP) .................................... 10008445

(51) Int. Cl.
- G01N 17/00 (2006.01)
- G01N 1/00 (2006.01)
- B01L 3/00 (2006.01)

(52) U.S. Cl. .................. 73/865.6; 73/863; 73/864.91

(58) Field of Classification Search ............... 73/432.1, 73/863, 864.91, 865.6
See application file for complete search history.

(56) References Cited

U.S. PATENT DOCUMENTS

| | | | |
|---|---|---|---|
| 2002/0100582 A1* | 8/2002 | Oldenburg | 165/253 |
| 2005/0281711 A1* | 12/2005 | Testa et al. | 422/100 |
| 2007/0183633 A1* | 8/2007 | Hoffmann | 382/116 |
| 2007/0234829 A1* | 10/2007 | Pirsch et al. | 73/865.6 |
| 2008/0236178 A1* | 10/2008 | Hosel et al. | 62/186 |
| 2009/0025287 A1 | 1/2009 | Lee | |
| 2009/0133514 A1* | 5/2009 | Murakami et al. | 73/865.6 |
| 2009/0310839 A1 | 12/2009 | Katzenelson et al. | |
| 2011/0205351 A1* | 8/2011 | Nakamura et al. | 348/79 |

FOREIGN PATENT DOCUMENTS

| | | |
|---|---|---|
| DE | 10 2006 043 117 B3 | 4/2008 |
| FR | 2 806 583 A1 | 9/2001 |
| WO | WO 93/13491 A1 | 7/1993 |

OTHER PUBLICATIONS

English Translation of Capelle, Hubert, French Patent No. FR 2806583 A1, dated Sep. 28, 2001, translated Apr. 2012.*

* cited by examiner

*Primary Examiner* — Hezron E Williams
*Assistant Examiner* — David Z Huang
(74) *Attorney, Agent, or Firm* — Rabin & Berdo, P.C.

(57) ABSTRACT

An apparatus for arranging at least one sample container inside an optical measuring device includes a carrier for arranging the sample container and a ventilation device. The ventilation device is arranged adjacent to the carrier and is provided with at least one air outlet arranged above the carrier. The ventilation device includes at least one heating element for generating an airflow and heating up the airflow.

20 Claims, 5 Drawing Sheets

APPARATUS, DEVICE AND METHOD FOR ARRANGING AT LEAST ONE SAMPLE CONTAINER

BACKGROUND OF THE INVENTION

1. Technical Field

The invention relates to an apparatus for arranging at least one sample container in an optical measuring device, an optical measuring device including such an apparatus, and the use of such an optical measuring device.

2. Related Art

In the biological and pharmaceutical research field, methods for measuring the fluorescence and luminescence have been used successfully for many years. For this, transfected or transgenic animals or plants are used, where at least one gene of the respective plant or the respective animal can code a protein that shows luminescence or fluorescence. If the gene is active, this protein is formed and conclusions can be reached relating to the activity of the respective gene by observing its luminescence or fluorescence. For example, conclusions also can be reached concerning the effect which specific substances have on the animal/the plant. Measuring the luminescence and/or the fluorescence activity can be realized integrally or with a local resolution.

In particular, in plants, the expression of many of these genes is subject to a circadian rhythm or is dependent on growth phases. Both can in turn be influenced through external influences of natural or artificial origin. The gene expressions are therefore tracked over longer periods of time (ranging from several hours to several weeks).

The sample containers, for example, Petri dishes, are at least sealed and at times also sterilized and sealed to prevent unintended contamination of the sample material, meaning the plants or seedlings. This is normally achieved with transparent lids which are additionally secured with adhesive tape or a layer of paraffin wax. The samples inside the sample containers are normally positioned in or on top of an aqueous liquid or a solid medium.

At least one sample container is positioned on a carrier which can be a simple plate or board. A carrier of this type is provided with depressions or the like to always ensure the same measuring positions, especially if several sample containers are used, so that the carrier determines a geometric arrangement of the sample containers. For the sake of simplicity, we always refer to several sample containers in the following, but it is clear that only a single sample container may exist.

The luminescence or fluorescence is usually measured with the aid of an optical sensor unit—at least one photomultiplier or a sensitive CCD (charge-coupled device) camera—which is located above the sample container.

It is an object of the present invention to improve the state of the technology in such a way that the reproducibility of the luminescence and fluorescence measurements is improved.

It has turned out that during the operation of the optical measuring device, condensate can form on the lids of the sample containers. Condensation forming larger droplets will falsify the obtained measuring values as a result of scattering and/or absorption (refers to at least a fluorescence or luminescence measurement, but can also relate to a photographic recording). That is a serious problem for several reasons, specifically in long-term experiments where a sample container or a set of sample containers remain for several days or weeks inside the optical measuring device. If luminescence or fluorescence recordings are made, the optical sensor unit "does not see" the condensation droplets that have formed, especially if the unit operates without a local resolution. These droplets can also not be observed from the outside because a light-impermeable housing must exist for fluorescence and luminescence measuring operations. This means that a complete series of the measuring can be worthless and the measuring time is lost. What is even worse is if the condensate that forms evaporates again prior to the end of the series of the measuring because of changes in the conditions, especially a change in the temperature. In that case, it may not be noticed and a falsified measuring result will be used further.

SUMMARY OF THE INVENTION

According to the invention, a ventilation device with a heating element is therefore provided. This ventilation device is arranged such that it generates a heated airflow which is directed toward the lids or flows across the lids and can thus heat up the lids, thereby preventing the forming of condensate on the outsides or the insides of the lids or the sample containers.

According to the simplest embodiment of the invention, this ventilation device can operate continuously during a measuring operation and can be adjusted such that no condensate can form, regardless of the concretely existing conditions. However, this is a disadvantage in particular if the sample containers are cooled by the carrier since the cooling of the carrier in that case permanently counteracts the heating through the ventilation device. Consequently, it is preferable to provide a control circuit for activating the ventilation device and to adjust this circuit in such a way that the lid is heated just enough by the ventilation device, so that the temperature of the lids is always higher than the dew point of the air inside the sample containers and is always higher than the dew point of the air outside of the sample containers.

A controlled tempering of the sample containers and thus also the plants/seedlings should advantageously be possible via the tempering of the carrier, thus making it possible to simulate environmental conditions.

From known dew point curves, it is possible to deduce the conditions under which condensation occurs on a body surrounded by ambient air. The dew point or the dew point temperature is the temperature where a state of equilibrium is reached for an object (with the given humidity) between water condensation and water evaporation or, in other words, the temperature where condensation just starts. With a given pressure, the relative humidity of the air depends on the temperature. Air that is not completely saturated with water vapor has a relative humidity of less than 100% and can absorb further water vapor with unchanged temperature. If the temperature drops, the capacity of the air to absorb water vapor also decreases, meaning that with a given humidity, the relative humidity increases. At the dew point, a relative humidity of 100% is reached and condensation occurs. In the process, precipitation occurs at the solid or liquid surfaces, where the effect is stronger the lower the temperature at the interfaces, respectively the higher the humidity of the air. The dependence of the dew point on the temperature and the relative humidity can be derived from the known dew point curves.

To prevent condensation from forming on the lids of the sample containers, the temperature of the air flowing around the lids is selected such that with a given relative humidity of the ambient air on the inside or the outside, the temperature of the lids is always sufficiently above the dew point. However, the conditions can vary on the inside and on the outside of the Petri dish. It must be taken into consideration that the plants themselves are placed into an aqueous liquid or a solid medium and that the relative moisture content of the air inside the dish could reach up to 100% while the humidity on the outside, meaning in a housing that encloses a measuring device, is generally much lower. The higher dew point determines the minimum temperature of the lid which must be sufficiently above this dew point, so as to prevent the forming of condensation on the inside nor on the outside.

For example, we assume that the temperature inside a housing of the measuring device is 30° C., the relative humidity of the air is 50%, the temperature of the carrier on which the Petri dishes are located is 10° C., the air temperature inside the Petri dish and above the plants is 12° C., and the relative humidity is 90%. Based on the graph in FIG. 4, the dew point in the space outside of the Petri dish is 18° C. and the dew point for the inside space is 11° C. If the covering of the Petri dish is always held to a temperature above 18° C., no condensation can form on the outside and especially not on the inside.

The temperature of the airflow generated by the ventilation device is controlled such that the above condition is maintained with respect to the dew point.

The temperature of the lids is detected with the aid of a temperature sensor installed at a representative location and is used as actual value in a first control circuit and is constantly compared to the desired value. In case of deviations, the temperature is adjusted with the ventilation device.

DETAILED DESCRIPTION OF THE INVENTION

Figure 1:
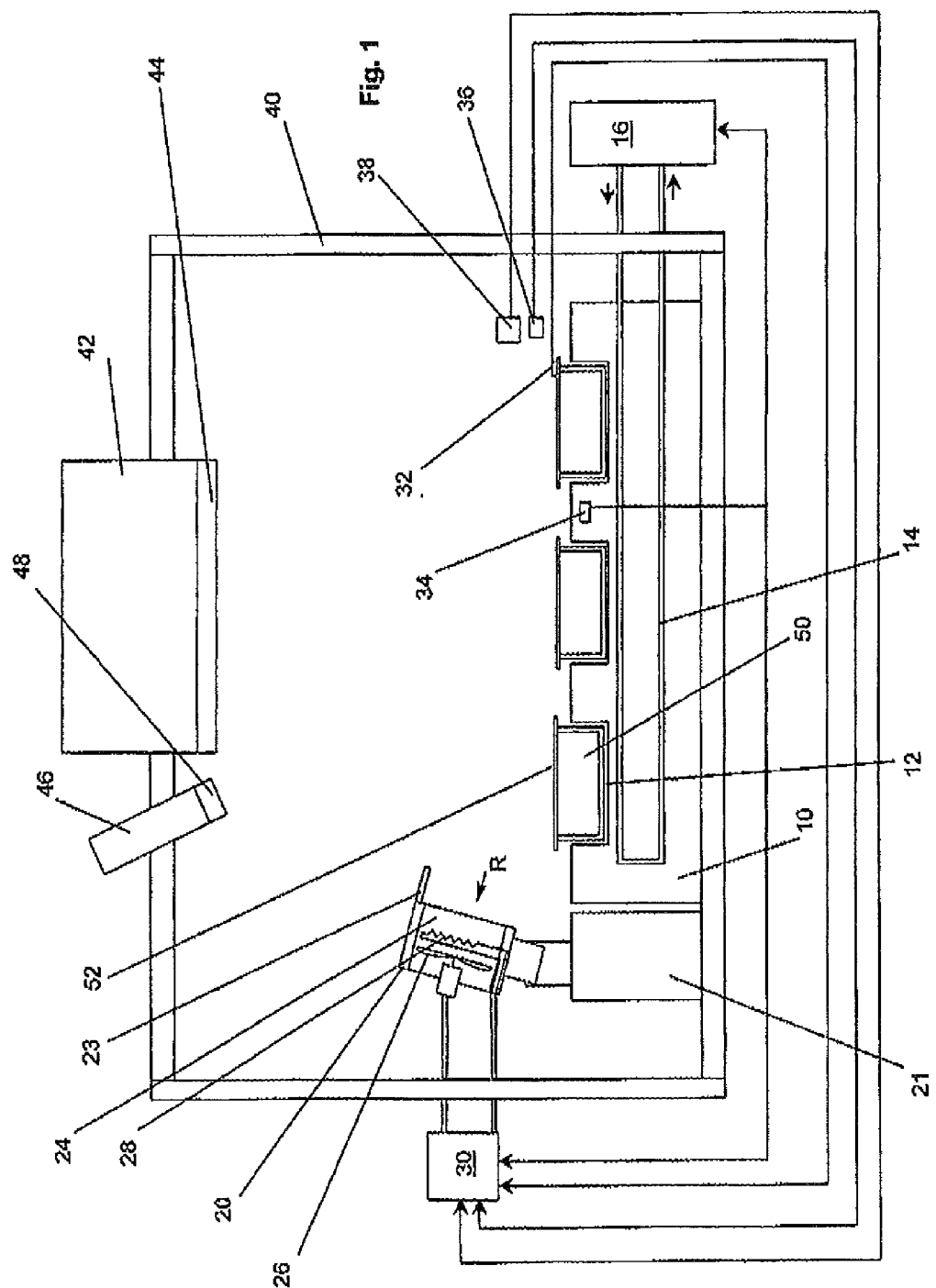
FIG. 1 is a schematic cross section through an optical measuring device with an apparatus according to the invention for arranging sample containers.

FIG. 1 shows an optical measuring device which is used for measuring luminescence and/or fluorescence of plants or seedlings inside sample containers 50 embodied as Petri dishes. As a rule, several such sample containers 50 are provided, for example 9 sample containers, where only three can be seen because of the sectional representation. The sample containers 50 are closed off with a lid 52 for the measuring operation.

The sample containers 50 are arranged on a carrier 10 which is provided with a depression 12 for each sample container. For the exemplary embodiment shown herein, the carrier 10 consists of metal, in particular aluminum, and has a correspondingly high thermal conductivity. Arranged above the carrier 10 is an optical measuring instrument, here taking the form of a camera and in particular a CCD camera 42, pointing in downward direction. An emissions filter 44 is arranged in front of the input window for this camera 42, of which the filter only allows light with a specific wavelength to penetrate and reach the camera 42. Furthermore provided is a light excitation source 46 which points in the direction of the carrier 10 and has an excitation filter 48 arranged in the beam path. The mode of operation of such a fluorometer is basically known and does not need to be explained in detail herein. Depending on the given geometry, it is possible on the one hand that the camera 42 can see all sample containers 50 at the same time, or that the carrier 10 and the camera 42 can be displaced relative to each other in horizontal direction, so that the camera can respectively only measure one sample container 50 (not shown). The same is true for the excitation light source 46. This light source can either be embodied to illuminate all sample containers 50 simultaneously, or it can be embodied such that only the sample container to be measured at the time is illuminated, where this case also requires a relative mobility between the excitation light source 46 and the carrier 10, and/or the excitation light source 46 must have the ability to pivot. The carrier 10, the light input window on the camera 42, and the outlet window for the excitation light source 46 are all located inside a light-impermeable housing 40.

The carrier 10 can be tempered so that the plants/seedlings inside the sample containers 50 can be observed at different and defined temperatures. For the exemplary embodiment, the carrier is tempered with the aid of a liquid cycle which is provided inside the carrier 10 with a heat exchanger 14 and outside the carrier 10 with a tempering device 16 for tempering the circulating liquid (mostly water), meaning as a rule it can be heated as well as cooled. Owing to the depressions 12 (for which the diameter essentially corresponds to the diameters of the sample containers 50), the temperature of the sample containers essentially reaches the same temperature as the carrier after a certain period of operation. It must be taken into consideration here that for reasons of a better overview a certain distance is drawn into the schematic representation between these sample containers 50 and the wall and the depressions 12, but that in reality the carrier 10 and the sample containers 50 of course are in direct contact, at least on the bottom of the sample containers 50. The clearance space on the side is preferably also kept as small as possible to establish the best possible thermal contact. This contact can be improved further by providing a liquid medium inside the depressions 12 so that no air gap remains. Instead of providing a heat exchanger, it is also possible to provide for direct electrical tempering of the carrier 10, namely with the aid of at least one electrical heating element and at least one Peltier cooler.

Figure 2:
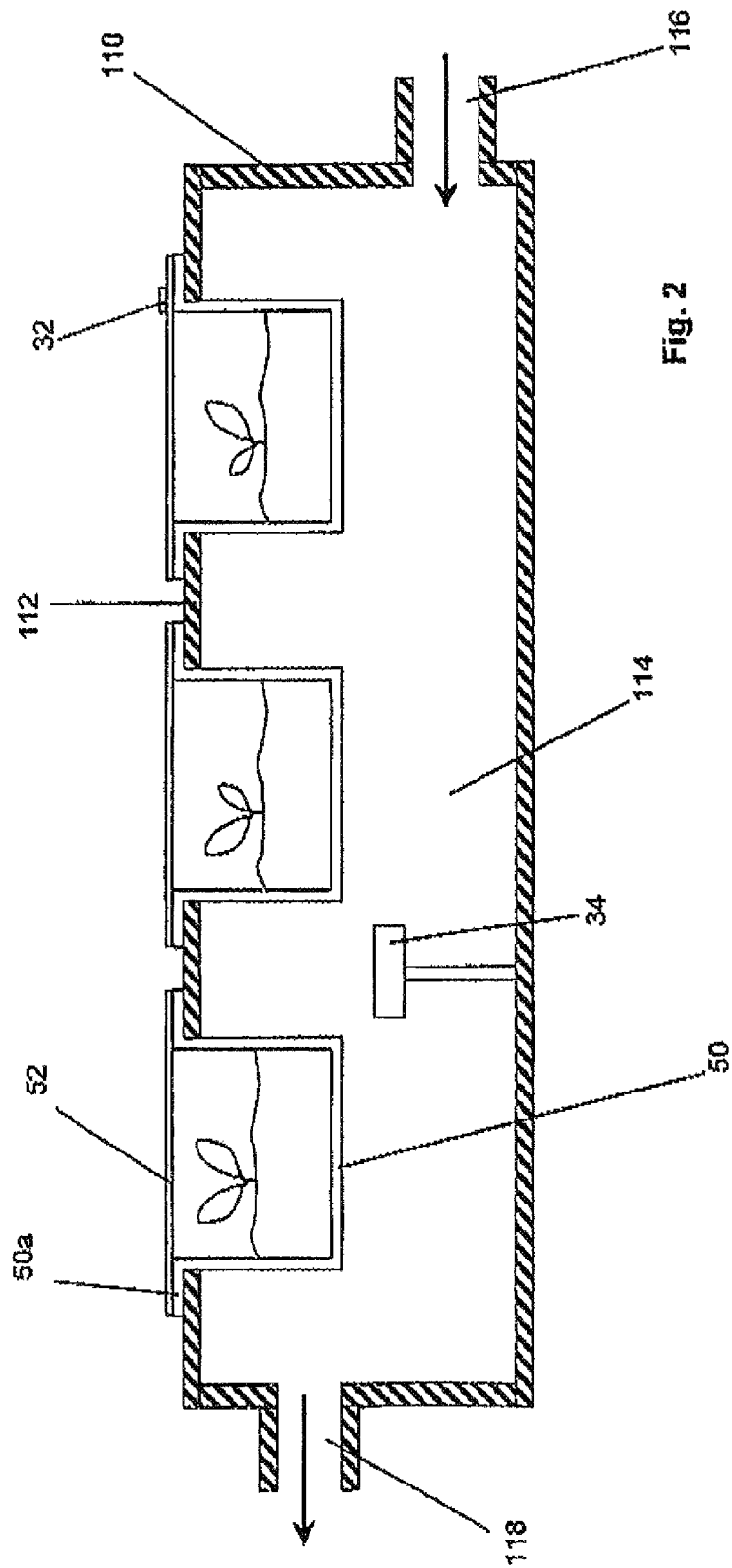
FIG. 2 is a alternative carrier with a tempering device.

FIG. 2 shows an alternative embodiment of a carrier which can be used for tempering the sample containers 50. In this case, the carrier is embodied as a housing-type carrier 110 which encloses a cavity 114. Tempered air can be supplied to this cavity 114 with the aid of an air feed-in 116. The tempered air flows through the cavity and leaves the cavity via an air outlet 118. The associated tempering device for the air is not shown herein. The top 112 of the housing-type carrier 110 is provided with openings through which the sample containers 50 project into the cavity 114, so that the sample containers 50 are tempered directly by the air flowing through the cavity 114 of the housing-type carrier 110. The sample containers in this case preferably have a collar which rests on the top side 112 of the housing-type carrier 110.

According to a different alternative embodiment, no separate carrier exists, but at least one sample container (which can also be rather large in this case) is placed directly onto the floor of the housing which then serves as carrier. The ambient air within the housing, for which the temperature is adjusted with the aid of a tempering device, is used in this case to temper the sample containers. This can be achieved with the aid of an external tempering device (similar to the embodiment shown in FIG. 2) or with a heating, cooling, or heat-exchanger element inside the housing.

However, it is not important how the carrier is concretely embodied, meaning whether the sample containers 50 are tempered via direct contact with a solid carrier or via the air. In the following, we therefore in general always refer to the temperature of the carrier or the temperature of the sample containers.

A temperature sensor, namely the second temperature sensor 34, is provided for regulating the temperature of the carrier 10 and thus also the temperature of the sample containers 50. The output of this sensor is connected to the tempering device, thereby resulting in a control circuit which is referred to herein as the second control circuit.

The air in the measuring chamber—meaning the air within the light-impermeable housing 40 above the carrier 10, 110—generally has a temperature which differs from that of the carrier 10, 110 (except for the above-mentioned second alternative embodiment) and is generally between the temperature of the carrier 10 and the temperature of the ambient air in the laboratory. The air temperature within the housing 22 can be higher or lower than the temperature of the carrier. Since it is important to know this temperature for the embodiment shown herein, a temperature sensor is therefore provided—here called the third temperature sensor—which measures this air temperature. This third temperature sensor 36 is preferably arranged relatively close to the carrier 10, 110 and above the carrier 10, 110. It is furthermore also important to know the moisture content of the air within the housing, for which a humidity sensor 38 is provided, preferably near the third temperature sensor 36.

Finally, since we still need the temperature of the lids 52 that seal the sample containers, a further temperature sensor is provided which is here referred to as the first temperature sensor 32. This first temperature sensor 32 makes contact with a lid 52. Insofar as only the temperature of a single lid 52 is measured, it is important to ensure that the temperature is measured on a suitably positioned lid, where this will be discussed in further detail later on. The lids 52 as a rule consist of an extremely thin material such as glass or plastic, so that we can generally assume that the temperature of the lid is nearly homogeneous. If this is not ensured, it may be necessary for some applications to measure the temperature of a lid 52 from the outside (as shown) as well as from the inside (not shown herein).

As previously mentioned, plants or seedlings (shown in FIG. 2) are located inside the sample containers 50, as well as an aqueous nutrient solution or nutrient soil. Owing to this aqueous nutrient solution/nutrient soil and because of the fact that the sample containers 50 are sealed tightly or nearly tightly with the lids 52, we can generally assume (and this will be the "most unfavorable case" for the following considerations) that the humidity inside the sample container is 100% or nearly 100%.

Figure 3:
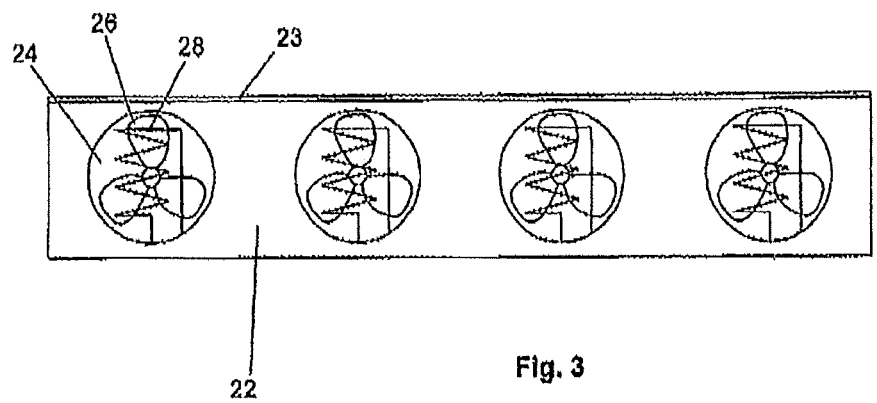
FIG. 3 is a view from above of the ventilation device shown in FIG. 1, as seen from the direction R.

It is an object of the present invention to provide a possibility where the camera 42 (meaning in general the optical sensor unit) can always view the plants and seedlings in the sample containers 50 under the same conditions. These desired same conditions can be hindered by condensation water that precipitates out on the lids 52, where this can occur on the outside or on the inside, depending on the given conditions. The ventilation device 20 (see FIGS. 1 and 3) is provided to prevent the forming of condensate in the described manner. The ventilation device 20 comprises a housing 22 with preferably several through openings 24. A fan 26 and a heating coil 28 are provided in each of these through openings 24. The width of the ventilation device 28 preferably matches substantially the width of the carrier 10, 110, so that an airflow generated by the ventilation device 20 for the most part arrives at and/or flows across all lids 52. A guide element 23 can be provided for improving the guidance of the generated airflow. The through opening 24—and thus also the air outlet openings of the ventilation device—are located above the carrier 10. The airflow generated by the ventilation device is directed from above and at a slant toward the tops of the lids, where all other sides of the sample containers are not affected.

The ventilation device 20 of course should not be located within the field of vision of the camera 42 and should not be installed in the light path for the excitation light source 4 and is consequently arranged next to the carrier 10. The ventilation device can be arranged directly on the carrier 10, in a separate holding unit 21 (as shown), or on the inside of the light-impermeable housing 40. As a rule, it is preferable if the ventilation device 20 points downward at an angle and it is furthermore also preferable if the angle of inclination is adjustable.

The ventilation device 20 must ensure that the temperature of the lids 52 is always above the dew point of the ambient air (meaning air directly above the lids) and the dew point of the air inside the sample containers.

Figure 4:
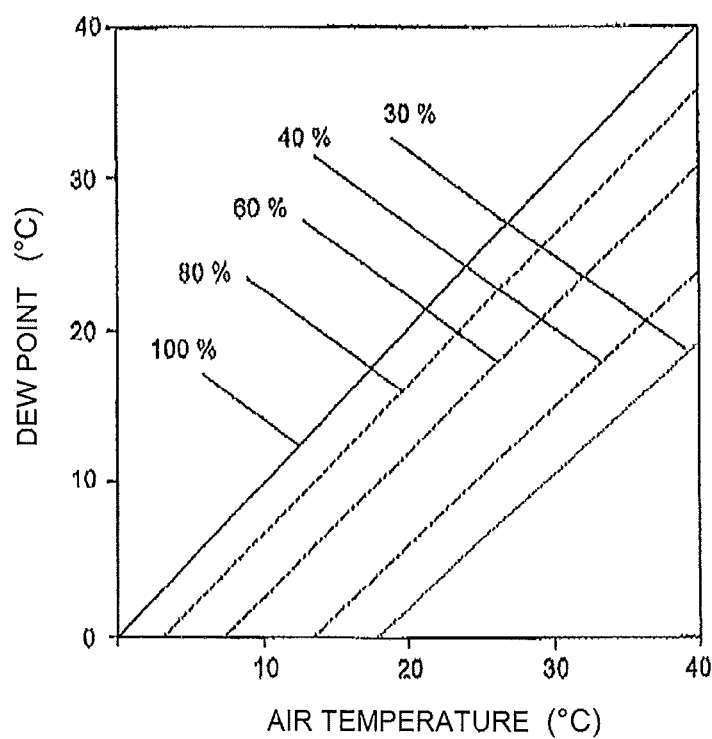
FIG. 4 is a diagram into which dew point lines have been drawn for different temperatures and humidity values.

The respective dew point temperatures are known and are shown with the examples in FIG. 4. In a very simple embodiment, the ventilation device could run permanently with constant air circulation and constant heat output and could be adjusted such that the lids 52 of each assumable configuration would be kept warm enough to prevent condensation. However, in most cases this is not a preferred option since the heating output in that case as a rule is much too high, which would have a negative effect on the tempering of the carrier and thus the sample containers. In particular if the sample containers are to be kept relatively cool, it is not advantageous, if they are heated permanently and strongly from above. A first control circuit is therefore advantageously provided which controls the ventilation device in such a way that the condensation of water on the lids is just prevented. That is to say, the temperature of the lids (insofar as this is needed at all) is held just slightly above the dew point by heating it with the aid of an airflow generated by the ventilation device. The first control circuit is now described as follows:

The first control circuit consists of the first temperature sensor 32, the second temperature sensor 34, the third temperature sensor 36, the humidity sensor 38 and the control unit 30 for the ventilation device. The first temperature sensor 32 measures, as shown in the above, the temperature of the lids 52 and as a rule the temperature of a representative lid. The temperature of a lid should be measured which has a tendency to be coldest and which for example as shown in FIG. 1 is positioned farthest away from the ventilation device. If this lid meets the necessary temperature criteria, it must be assumed that the remaining lids also meet these criteria. The air temperature inside the housing is furthermore measured constantly with the third temperature sensor 36, and the humidity inside the housing is measured with the humidity sensor 38. Based on this, the dew point of the measured air is automatically computed. The temperature of the carrier 10 is also measured permanently, where it is also assumed that this temperature essentially represents the temperature of the sample containers. Based on the further assumption that the humidity of the air inside the sample containers is at 100%, the dew point of this air is automatically computed and/or estimated. To be able to achieve a higher accuracy, it would be possible (with corresponding additional expenditure) to measure the temperature of a sample container or directly the temperature of the air inside a sample container. As described in the above, it is sufficient in most cases to have estimated values for the air temperature and the humidity in the sample container. These measurements are carried out continuously and the corresponding computations are processed, for example, by a microprocessor or the software of a connected computer. If the temperature of the lid approaches the higher of the two determined and/or estimated dew point temperatures less than a predetermined value, for example 1° C., then the control unit 30, to which the aforementioned values are supplied directly or indirectly, activates the ventilation device or respectively increases its actual output through a higher heating output and/or a higher air throughput. If the temperature of the lid subsequently surpasses a predetermined value, for example 2° C. more than the higher of the two dew point temperatures, the control unit shuts down the ventilation device or reduces its output. Thus, the temperature of the lids can be kept within a narrow temperature range, thereby reliably preventing on the one hand the forming of condensate and, on the other hand, keeping the heating output and the temperature difference between the lid and the sample container as low as possible.

It can be advantageous to keep the ventilation device running continuously and to only control the heating coil via the described control circuit.

Figure 6:
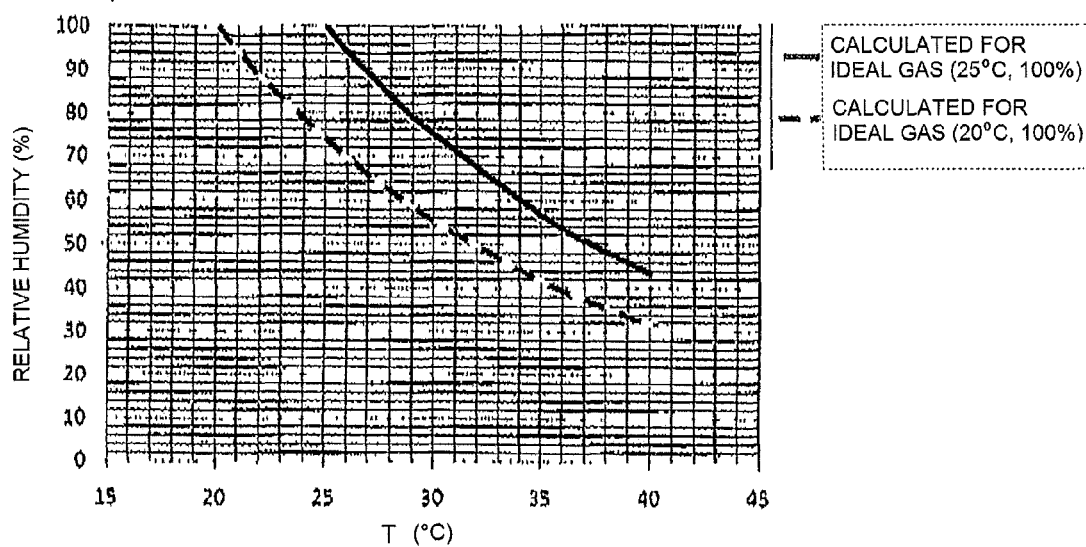
FIG. 6 is a diagram showing the dependence of the relative humidity on the temperature.

The physical background of the invention is easier to understand if we illustrate the dependence of the relative humidity on the temperature with the aid of the equation for an ideal gas. We recognize that in the range of the water vapor saturation, meaning a relative humidity of 100%, even the smallest temperature changes already change the relative humidity by several percentage points. With the example of FIG. 6 and a dew point of 25° C., a temperature increase of 1° C. is already sufficient to lower the relative humidity by 6%. Owing to the fact that the lid of each sample container is heated, no water vapor saturation exists in the adjacent air layer and condensation is prevented.

A distinction consequently should be made between the following two cases:
 a) The temperature of the sample container is raised relative to the ambient temperature;
 b) The temperature of the sample container is lowered relative to the ambient temperature.

In the first case, the tempering with the air arriving from the ventilation device and flowing over the lids requires the selection of a temperature that is higher than the temperature of the sample container since otherwise, at 100% relative humidity, the moisture condensates on the inside of the lid.

In the second case, it is sufficient to select the temperature for the tempering such that the lid temperature does not drop below the ambient temperature, so as to prevent condensation on the inside and on the outside.

As an example for the first case, we assume that the sample container is located inside a housing of the measuring device for which the temperature is assumed to be 23° C. and the relative humidity 50%. The carrier on which the sample containers, e.g. the Petri dishes, are located is set to 30° C. and the temperature of the air in the Petri dishes above the plants reaches 29° C. with a relative humidity of 100%. Based on the previous statements, the temperature on the inside of the lids must now be raised to >30° C. to avoid condensation.

The dew point for the outside is at 12° C. which is far away from the assumed temperature of 23° C. inside the housing of the measuring device.

Figure 5:
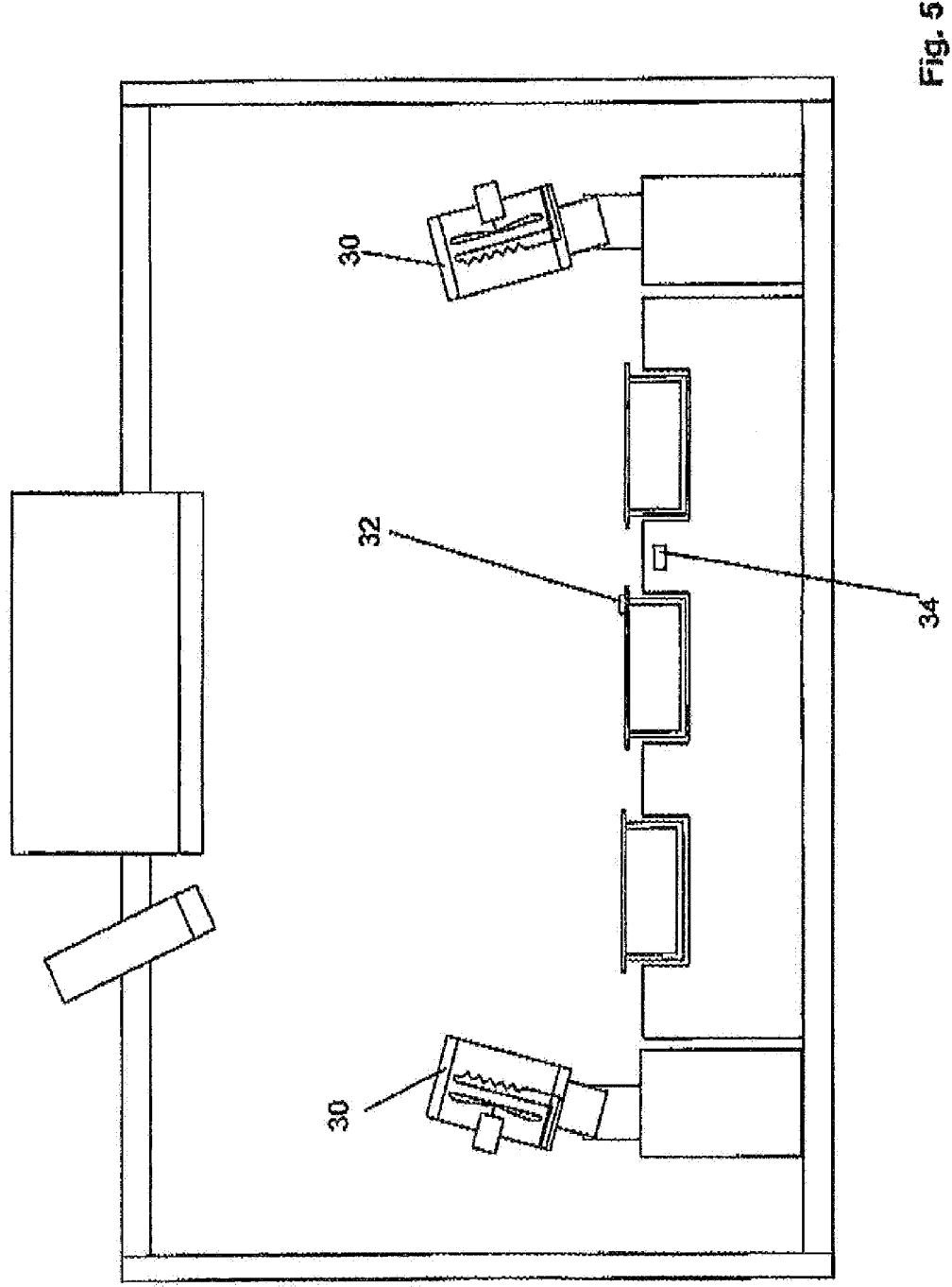
FIG. 5 is a second exemplary embodiment of the invention in a representation that corresponds to the one shown in FIG. 1.

As shown in FIG. 5, it is also possible to provide more than one ventilation device 20, where these two ventilation devices 20 in particular can be arranged on opposite sides of the carrier 10. Such an arrangement can make sense in particular for very large carriers in order to adjust nearly the same temperature on all lids 52.

The invention was explained with reference to measurements of plants and seedlings, but can also be used for realizing measurements for other organisms, in particular bacteria, small animals or embryos and cell cultures. The sample containers can furthermore also be embodied differently from the aforementioned Petri dishes. In particular, it is also possible to use so-called micro plates, meaning plates provided with a plurality of depressions. In that case, each depression forms a sample container.

What is claimed is:

1. An apparatus for arranging at least one sample container inside an optical measuring device, comprising:
 a carrier for positioning the at least one sample container;
 at least one ventilation device provided with at least one air outlet arranged above the carrier and arranged on the carrier or adjacent to the carrier, the at least one ventilation device including a heating element for generating an airflow and heating up the airflow; and
 a first control circuit for activating the heating element of the at least one ventilation device, the first control circuit including at least one first temperature sensor for measuring the temperature of a transparent lid that seals a first of the at least one sample containers.

2. The apparatus according to claim 1, wherein the first control circuit is laid out such that the temperature of the lid is always above the dew point of the air inside the first sample container because of the airflow supplied by the ventilation device.

3. The apparatus according to claim 1, further comprising:
 a tempering device for tempering the at least one sample container.

4. The apparatus according to claim 3, wherein the tempering device permits heating as well as cooling of the at least one sample container, relative to the ambient temperature.

5. The apparatus according to claim 3, further comprising:
 a second temperature sensor for measuring the temperature on the inside of a measured sample container of the at least one sample container, wherein the second temperature sensor is arranged on the measured sample container or the carrier,
 wherein the second temperature sensor is a component of the first control circuit.

6. The apparatus according to claim 3, wherein the carrier is equipped with the tempering device or is thermally connected thereto.

7. The apparatus according to claim 6, further comprising:
 a second temperature sensor for measuring the temperature on the inside of a measured sample container of the at least one sample container, wherein the second temperature sensor is arranged on the measured sample container or the carrier,
 wherein the second temperature sensor is a component of the first control circuit.

8. The apparatus according to claim 6, wherein the tempering device permits heating as well as cooling of the at least one sample container, relative to the ambient temperature.

9. The apparatus according to claim 8, further comprising:
 a second temperature sensor for measuring the temperature on the inside of a measured sample container of the at least one sample container, wherein the second temperature sensor is arranged on the measured sample container or the carrier,
 wherein the second temperature sensor is a component of the first control circuit.

10. The apparatus according to claim 9, further comprising:
a second control circuit for activating the tempering device, the second control circuit including the second temperature sensor.

11. The apparatus according to claim 9, wherein the first control circuit is laid out such that the temperature of the lid is always above the dew point of the air inside the first sample container because of the airflow supplied by the ventilation device.

12. The apparatus according to claim 11, further comprising:
a second control circuit for activating the tempering device, the second control circuit including the second temperature sensor.

13. The apparatus according to claim 11, further comprising:
a third temperature sensor, that is arranged above the carrier, which is part of the first control circuit,
wherein the first control circuit is laid out such that the temperature of the lid is always above the dew point of the air measured by the third temperature sensor as a result of the airflow that is supplied by the ventilation device.

14. The apparatus according to claim 13, further comprising:
a humidity sensor provided above the carrier for measuring the humidity in the air,
wherein this humidity sensor is part of the first control circuit.

15. The apparatus according to claim 1, wherein at least two ventilation devices are provided.

16. An optical measuring device, comprising:
the apparatus according to claim 1; and
an optical sensor unit for which an input window is located above the carrier.

17. The optical measuring device according to claim 16, wherein the carrier and the ventilation device are arranged inside a light-impermeable housing.

18. The optical measuring device according to claim 16, wherein the optical sensor unit is embodied as one of a luminometer and a fluorometer.

19. A method for preventing the forming of condensate on the outside or inside of a sample container in an optical measuring device, the sample container being sealed by a lid, the method comprising the steps of:
generating an airflow which is directed toward the lid or flows across the lid;
measuring a temperature of the lid, a temperature on the inside of the sample container, and a temperature of air;
heating up the airflow so that the measured temperature of the lid is higher than the dew point of the air inside the sample container and is higher than the dew point of the air outside the sample containers;
measuring a humidity value in air;
computing a particular dew point when a particular temperature and a particular relative humidity value are given, by deriving a dependence relationship of the particular dew point on the particular temperature and the particular relative humidity from known dew point curves;
comparing the measured temperature of the lid with a desired temperature; and
adjusting a temperature for heating up the lid when the measured actual temperature of the lid deviates from the desired temperature.

20. The method of claim 19, further comprising determining the desired temperature from the particular dew point.

* * * * *